United States Patent [19]

Shepherd

[11] Patent Number: 5,026,854
[45] Date of Patent: Jun. 25, 1991

[54] METHOD FOR THE PRODUCTION OF 2-BROMO-5,6,7,8-TETRAHYDROQUINOLINE AND THE ANALOGOUS 2-BROMO-TRIMETHYLENE AND PENTAMETHYLENE PYRIDINES

[75] Inventor: Robin G. Shepherd, Windsor, United Kingdom

[73] Assignee: John Wyeth & Brother Limited, Maidenhead, England

[21] Appl. No.: 564,264

[22] Filed: Aug. 8, 1990

Related U.S. Application Data

[62] Division of Ser. No. 367,531, Jun. 16, 1989, Pat. No. 4,975,431.

[30] Foreign Application Priority Data

Jun. 17, 1988 [GB] United Kingdom ............... 8814458

[51] Int. Cl.$^5$ ............... C07D 215/18; C07D 231/04
[52] U.S. Cl. ............................... 546/112; 546/153; 546/170; 546/173; 546/174; 546/180
[58] Field of Search ............... 546/180, 112, 153, 170, 546/173, 174

[56] References Cited

PUBLICATIONS

Chemical Abstracts, vol. 59, 6364c (1963); Hahn et al., Roczniki Chem. vol. 37, pp. 109–112 (1963).
Chemical Abstracts, vol. 89, 197349n (1978); Mishima et al., Japan. Kokai 78 68,788, Jun. 1978.

Primary Examiner—Bernard I. Dentz
Attorney, Agent, or Firm—George Tarnowski

[57] ABSTRACT

The invention concerns compounds of formula I

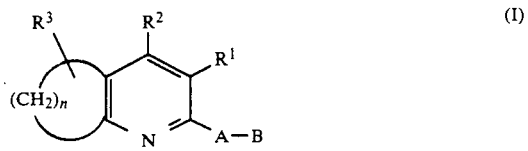

or a salt thereof, wherein $R^1$ and $R^2$ each independently represent hydrogen, lower alkyl, lower alkoxy, carboxyloweralkyl, carboxy, hydroxyloweralkyl, halogen, haloloweralkyl, lower alkoxycarbonyl, optionally substituted aryl or optionally substituted aralkyl, n represents an integer from 3 to 6; $R^3$ which is optionally present represents single or multiple substitution on one or more of the aliphatic carbons by one or more substituents selected from lower alkyl, optionally substituted aryl and optionally substituted aralkyl; A represents a group of formula (i) or (ii) below:

$$-CR^4R^5-(CR^6R^7)_m- \qquad (i)$$

$$-CX-(CR^6R^7)_m- \qquad (ii)$$

in which $R^4$, $R^6$ and $R^7$ each independently represent hydrogen or lower alkyl (providing that when $R^5$ is $NH_2$, $R^4$ is hydrogen); m is 0 or 1; $R^5$ represents hydrogen, $NH_2$, OH or loweralkoxy, and X is $=O$, $=NH$ or $=NOH$, the attachment of A to B being from either end, and B represents an optionally substituted aryl or heteroaryl radical which compounds possess anti-inflammatory activity. Also disclosed is a process for preparing a useful intermediate to compounds of formula I.

1 Claim, No Drawings

METHOD FOR THE PRODUCTION OF 2-BROMO-5,6,7,8-TETRAHYDROQUINOLINE AND THE ANALOGOUS 2-BROMO-TRIMETHYLENE AND PENTAMETHYLENE PYRIDINES

This is a division of application Ser. No. 07/367,531 filed June 16, 1989 now U.S. Pat. No. 4,975,431.

This invention relates to heterocyclic compounds, more particularly to pyridine derivatives, processes for preparing them, pharmaceutical compositions containing them and to intermediates therefor.

This invention provides compounds of formula

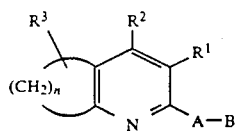

or a salt thereof, wherein $R^1$ and $R^2$ each independently represent hydrogen, alkyl, alkoxy, carboxyalkyl, carboxy, hydroxyalkyl, halogen, haloalkyl, alkoxycarbonyl, optionally substituted aryl or optionally substituted aralkyl, n represents an integer from 3 to 6; $R^3$ which is optionally present represents single or multiple substitution on one or more of the aliphatic carbons, eg. by one or more substituents selected from lower alkyl, optionally substituted aryl and optionally substituted aralkyl; A represents a group of formula (i) or (ii) below:

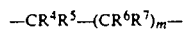

in which $R^4$, $R^6$ and $R^7$ each independently represent hydrogen or lower alkyl (providing that when $R^5$ is $NH_2$ $R^4$ is hydrogen); m is 0 or 1; $R^5$ represents hydrogen, $NH_2$, OH or loweralkoxy, and X is =O, =NH or =NOH, the attachment of A to B being from either end; and B represents an optionally substituted aryl or heteroaryl radical.

By the term aryl as used herein is meant any monovalent carbocyclic radical possessing aromatic character and includes groups having 6 to 10 carbon atoms such as phenyl and naphthyl. By the term heteroaryl as used herein is meant any monovalent heterocyclic group possessing aromatic character and includes groups having 5 to 10 ring atoms and one or more heteroatoms selected from oxygen, nitrogen and sulphur. Examples of heteroaryl radicals are furyl, thienyl, pyrrolyl, pyridinyl, pyrimidinyl, quinolyl, isoquinolyl, benzimidazolyl, thiazolyl and imidazolyl.

The term alkyl when used to signify a group or part of a group such as hydroxyalkyl or aralkyl means any straight or branched saturated aliphatic hydrocarbon especially those having 1 to 6 carbon atoms, eg. 1–4 carbon atoms. Examples are methyl, ethyl, n-propyl, isopropyl, n-butyl, n-pentyl and n-hexyl.

By the term 'optionally' substituted is meant optional substitution on carbon atoms by one or more substituents, eg. substituents commonly used in pharmaceutical chemistry, eg. halogen (eg. Cl,Br,F), alkyl, alkyloxy, haloalkyl (eg. $CF_3$), or haloalkoxy (eg. $CHF_2O-$, $CF_3CH_2O-$), $NO_2$, $NH_2$, CN, alkylamino, dialkylamino, carboxy, alkyloxycarbonyl, acyl, acylamino, aryl, (eg. phenyl) or aminoalkyl.

The term 'lower' as used herein to qualify a group means such a group contains 1 to 6 carbon atoms.

Examples of the groups $R^1$ and $R^2$ are independently hydrogen, lower alkyl (eg. methyl, ethyl, n-propyl, isopropyl, n-butyl, n-pentyl and n-hexyl), —COOH, —COOlower alkyl (eg. COOMe, COOEt), —$CH_2OH$, Br, Cl, $CF_3$, OMe, optionally substituted phenyl or optionally substituted benzyl.

Preferred values of n are 3,4, or 5 such that the compounds have one of the following formulae

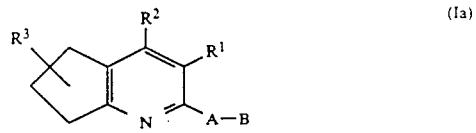

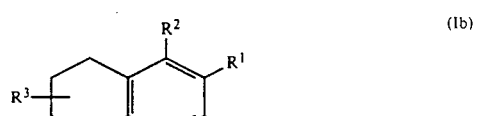

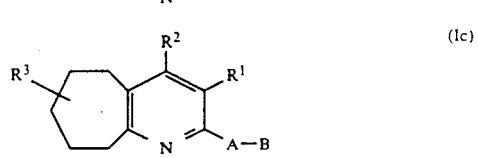

Compounds of formula Ic are most preferred.

Examples of $R^3$ are one or more substituents selected from methyl, ethyl, methoxy, ethoxy, phenyl, phenyl substituted by halogen, lower alkyl or lower alkoxy, benzyl and benzyl substituted by halogen, lower alkyl or lower alkoxy. Examples of multisubstitution on one carbon atom is gem-dimethyl.

Examples of $R^4$, $R^6$ and $R^7$ are independently hydrogen, methyl and ethyl.

The linkage of —A— to the pyridine ring and B can be either way round so that examples of —A—B are —CHOH—B, —CHOHCH₂—B, —CH₂CHOH—B, —CO—B, —COCH₂B, —CH₂COB, —CH(OCH₃)—B, —CH(OCH₃)CH₂B and —CH₂CH(OCH₃)—B. Preferably A is —CHOH— or —CO—.

Examples of B are phenyl, pyridyl (eg. pyrid-2-yl), 1-naphthyl, 2-naphthyl which groups may be substituted as defined herein, for example by one or more substituents selected from lower alkyl, lower alkoxy, halogen, haloloweralkyl, nitro, amino, lower alkylamino, cyano, carboxy, lower alkoxycarbonyl and lower alkylcarbonyl.

In a preferred aspect this invention provides compounds of formula

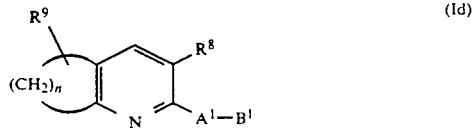

or salts thereof,
wherein n represents 4 or 5; $R^8$ represents lower alkyl, halogen, carboxy, loweralkoxy; $R^9$ represents hydrogen or a lower alkyl group; $A^1$ represents —CO— or —CHOH— and B¹ represents optionally substituted phenyl, especially where the substituent is selected from one or more of the following: lower alkyl, (eg. o-,m-or p-methyl); halogen (eg. o-,m-or p-chloro or bromo); lower alkoxy (eg. o-,m- or p-methoxy), and carboxy, eg. o-,m- or p-carboxy. Other examples of B¹ (and B) include 2,4-dimethylphenyl; 3,4-dimethylphenyl 4-ethylphenyl; 4-isopropylphenyl, 4-isobutylphenyl. 2-methoxy-4-methylphenyl, 2-chloro-4-methylphenyl.

The compounds of formula I can possess one or more asymmetric centres and hence optical isomers and mixtures thereof are possible, eg. when A is CHOH or R³ represents monosubstitution. All such isomers and mixtures thereof are included within the scope of this invention. Where any reaction process produces mixtures of such isomers standard resolution techniques may be applied to separate a specific isomer.

The compounds of formula I may be obtained in free base form or as acid addition salts as desired. Examples of such salts include salts with pharmaceutically acceptable acids such as hydrochloric, hydrobromic, hydroiodic, sulphuric, phosphoric, nitric, acetic, citric, tartaric, fumaric, succinic, malonic, formic, maleic acid or organosulphonic acids such as methane sulphonic or p-toluene sulphonic acids.

When acidic substituents are present it is also possible to form salts with bases eg. alkali metals (such as sodium) or ammonium salts. Such salts of the compounds of formula I are included within the scope of this invention.

When basic substituents are present then quaternary ammonium salts may be formed by quaternizing with an alkylating agent such as alkyl, or alkyl halides.

The compounds of formula I possess pharmaceutical activity in standard tests, in particular anti-inflammatory activity. Anti-inflammatory compounds of the non-steroidal type currently available generally have a tendency to cause gastric irritation and some are markedly ulcerogenic. It has surprisingly been found that in standard tests compounds of formula I appear to be devoid of ulcerogenic properties even at high doses.

The compounds of formula I were tested for anti-inflammatory activity in the following test procedures:

PROCEDURE 1

Anti-inflammatory activity of a compound is assessed by its ability to inhibit experimentally induced edema in the hind paw of the rat.

Groups of six male Sprague-Dawley rats (Charles River), weighing between 150–165 g, were used in these experiments. Drugs were administered p.o. in 0.5% methylcellulose (400 centipoise). One hour after administering drugs or vehicle, 0.1 ml of 1% carrageenan was injected subplantar into the right hind paw. Right hind paw volumes (ml) were measured prior to carrageenan injection using a mercury plethysmograph (ie. zero time reading). After three hours, the right hind paw volumes were re-measured and paw edema was calculated for each rat by subtracting the zero time reading from the three hour reading. The percent change in paw edema was calculated according to the formula:

$$\% \text{ Inhibition} = 100\% \times \frac{\text{Mean vol. swelling control} - \text{mean vol. swelling of test}}{\text{Mean vol. swelling of control}}$$

The Dunnett's test was used to determine statistical significance (P<0.05).

In the above test representative compounds of formula I gave the results shown in TABLE I.

TABLE 1

| Compounds of formula I Dose 50 mgs/kg | Mean Paw Edema @ 3 hours ml + S.E | Number of Assays | Average % change @ +3 hours |
|---|---|---|---|
| Control | 1.1 ± 0.05 | 100 | — |
| 1-(6,7,8,9-Tetrahydro-3-methyl-5H-cyclohepta[b]-pyrid-2-yl)-1-(4-methylphenyl)methanol(Example 1) | 0.45 ± 0.06 | 2 | −59 |
| 6,7,8,9,-Tetrahydro-3-methyl-2-(methyl-benzoyl)-5H-cyclohepta[b]pyridine, hydrochloride (Example 2) | 0.47 ± 0.05 | 2 | −58 |
| 1-(6,7,8,9-Tetrahydro-5H-cyclohepta[b]pyrid-2-yl)-1-(4-methylphenyl)methanol (Example 3) | 0.83 ± 0.06 | 2 | −24 |
| 1-(6,7,8,9-Tetrahydro-3-methyl-5H-cyclohepta[b]pyrid-2-yl)1-phenylmethanol | 0.51 ± 0.08 | 2 | −54 |

Compounds which inhibit the swelling by about 20% are considered of interest. The results show that all the compounds were active with the compounds of Examples 1,3 and 4 demonstrating marked anti-inflammatory activity at the dose level tested.

PROCEDURE 2

In this procedure polyarthritis is induced in male Lewis strain rats by the injection of a tubercle bacilli in the subplanter tissue of the right hind paw.

Groups of ten male Lewis rats (Charles River), weighing between 150–170 g, were injected s.c. into the right hind paw with dessicated *Mycobacterium butyricum* (0.5 mg/0.1 ml) suspended in light mineral oil. Drugs were administered orally in 0.5% methylcellulose from day 0 to 15 (except weekends). Both hind paw volumes (ml) were measured by mercury plethysmography at the time of injection of adjuvant (day 0). Paw volumes were measured on day 4 (injected paw only) and on day 16 (uninjected paw) to determine the non-specific and immunologically-induced inflammation, respectively. Drug effects were expressed as a percentage change from vehicle-treated arthritic controls.

Active compounds will either prevent or reverse the joint swelling and associated sequella of polyarthritis. A % change of about 20% from control is regarded as noteworthy.

In this test in a series of experiments compounds of formula I gave the results shown in Table 2.

TABLE 2

| Compound of formula I | Dose level | % Change from Control |
|---|---|---|
| 1-(6,7,8,9-tetrahydro-3-methyl-5H-cyclohepta[b]-pyrid-2-yl)-1-(4-methylphenyl)methanol | 30 mg/kg | −47% |
| 6,7,8,9-tetrahydro-3-methyl-2-(4-methylbenzoyl)-5H-cyclohepta[b]pyridine, hydrochloride | 30 mg/kg | −26% |
| 1-(6,7,8,9-tetrahydro-5H- | 30 mg/kg | −33% |

TABLE 2-continued

| Compound of formula I | Dose level | % Change from Control |
|---|---|---|
| cyclohepta[b]-pyrid-2-yl)1-(4-methylphenyl) methanol | | |
| 1-(6,7,8,9-tetrahydro-3-methyl-5H-cyclohepta[b]-pyrid-2-yl)-1-phenyl-methanol | 30 mg/kg | −45% |

The results in Table 2 show the above-mentioned compounds of formula I exhibit marked antiflammatory activity in the test.

In standard tests investigating gastric irritation representative compounds of formula I, namely 1-(6,7,8,9-tetrahydro-3-methyl-5H-cyclohepta[ b]pyrid-2-yl)-1-(4-methylphenyl)methanol and 6,7,8,9-tetrahydro-3-methyl-2-(4-methylbenzoyl)-5H-cyclohepta[b]pyridine, hydrochloride did not show any effect at the highest dose level tested of 300 mg/kg.

The compounds of formula I may be prepared by various methods all of which are included in the scope of this invention.

A first method for preparing compounds of formula I wherein A is $-CR^4R^5-(CR^6R^7)_m-$ where $R^5$ is OH and $R^4$, $R^6$, $R^7$ and m are as defined above comprises reacting a compound of formula

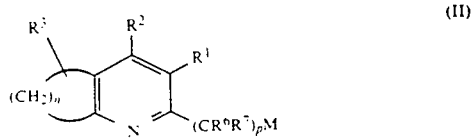
(II)

wherein $R^1$, $R^2$, $R^3$ and n are as defined above, p is 0 or 1 and M is sodium, potassium, lithium, Mghal where hal is halogen, eg. chlorine, bromine or iodine providing that hal is not chlorine when p is 0, with a compound of formula

(III)

wherein B, $R^3$, $R^6$ and $R^7$ are as defined above and q is 0 or 1 providing that p+q is 0 or 1, followed by protonation.

The reaction is conveniently carried out under anhydrous conditions in an appropriate inert solvent eg. tetrahydrofuran, toluene, diethyl ether, an alkane (such as hexane) or a cycloalkane (eg. cyclohexane) or mixtures of such solvents at or below room temperature. Preferably the starting material of formula II is prepared in situ and the same solvent used for reaction with the compound of formula III. The final step in the reaction is to protonate the intermediate complex, eg using water alcohol or an acid. In the aforementioned reaction any carbon atom epi to the nitrogen (for example the 9-position when n is 5) may be protected prior to reaction for example by using one or two organic silyl protecting groups, eg. trialkylsilyl such as trimethylsilyl and removing the protecting group(s) after the reaction.

The starting material of formula II may generally be prepared by metallation reactions from appropriate corresponding compounds of formula

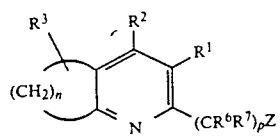
(IV)

optionally protected in the epi position where Z is hydrogen or halogen and n,p,$R^1$,$R^2$, $R^3$ and $R^6$ and $R^7$ are as defined above. For example the starting material of formula II wherein M is lithium, sodium or potassium may be prepared by reacting a compound of formula IV wherein Z is hydrogen or bromine or iodine with a metal alkyl, eg. $MR^{10}$ wherein M is Li, Na or K and $R^{10}$ is alkyl, aryl or aralkyl, for example n-butylithium. Compounds of formula II where M is Mghal may be prepared by treating a compound of formula IV wherein Z is halogen with magnesium under conditions known for the preparation of Grignard reagents.

Compounds of formula IV are known compounds or can be made by known methods for analogous compounds. For example 5,6,7,8-tetrahydroquinolines can be prepared by reacting 3-aminoacroleins with cyclohexanones according to the method of Breitmaier and Bayer (Tet Letts 1970, 38, 3291). Similarly 6,7,8,9-tetrahydro-5H-cyclohepta[b]pyridines and cyclopenta[b]pyridines can be prepared by reacting respective cycloheptanone or cyclopentanones with 3-aminoacroleins (eg. 3-amino-2-methylacrolein). These and other methods are described in UK Patent Specification 1,432,378.

Another aspect of this invention provides a new and particularly convenient route to compounds of formula IV wherein p is O and Z represents bromine. Such compounds may be prepared by reacting a compound of formula

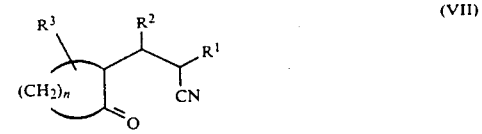
(VII)

wherein n,$R^1$,$R^2$ and $R^3$ are as defined above with either bromine or HBr and bromine in an inert solvent, such as an alkanoic acid eg. acetic acid or halocarbon, eg. methylene dichloride. This is believed to be the first direct cyclisation route to 2-bromo-cycloalkenopyridines. Previously such compounds were prepared by halogenating a corresponding 2-hydroxypyridine. The new process provides a particularly useful route via the appropriate intermediates ultimately to compounds of formula I wherein n=5. The reaction may be carried out without heating if desired using approximately equimolar quantities of bromine and compound of formula VII. When HBr is used the amount may vary from a catalytic amount to a molar excess, eg. 5M.

A further aspect of this invention provides intermediates of formulae II and IV wherein n is 5.

Compounds of formula I wherein A is $-CX-(CR^6R^7)_m-$ where X is $=NH$ and m, $R^6$ and $R^7$ are as defined above may be prepared by reacting a compound of formula:

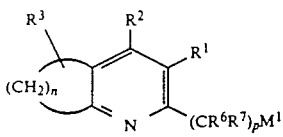 (V)

(if required protected in the epi position) wherein n, $R^1, R^2$ and $R^3$ are as defined above, p is 0 or 1 and $M^1$ is lithium, sodium, potassium or Mghal where hal is chlorine, bromine or iodine, with a nitrile of formula:

$$B(CR^6R^7)_qCN \qquad (VI)$$

wherein B, $R^6$ and $R^7$ are as defined above and q is 0 or 1 providing that $p+q=0$ or 1 and if required removing any protecting group. The above reaction may be conveniently carried out at or below room temperature in an inert solvent under anhydrous conditions.

Compounds of formula I wherein A is $-CR^4R^5-(CR^6R^7)_m-$ wherein $R^5$ is amino, $R^4$ is hydrogen and m, $R^6$ and $R^7$ are as defined above, may be prepared by a process which comprises reducing a corresponding compound of formula I wherein A is $-CX-(CR^6R^7)_m-$ where X is $=NH$. The reduction is conveniently carried out using an alkali metal borohydride, such as sodium borohydride in alcohol solvent, eg. ethanol.

Compounds of formula I wherein A is $-CO-(CR^6R^7)_m-$ where m, $R^6$ and $R^7$ are as defined above may be prepared by a process which comprises
a) hydrolysing a compound of formula I wherein A is $-CX-(CR^6R^7)_m-$ where X is $=NH$ or $=NOH$, or
(b) oxidising a compound of formula I wherein A is $-CR^4R^5-(CR^6R^7)_m-$ wherein $R^4$ is hydrogen, $R^5$ is OH and m, $R^6$ and $R^7$ are as hereinbefore defined. The hydrolysis step (a) may be carried out using an aqueous acid with heating. The oxidation step (b) may be carried out using an oxidation agent known for oxidising alcohols to ketones, eg. manganese dioxide.

Where the product of a reaction is a ketone then the oxime derivative thereof may de prepared in the usual manner eg. using hydroxylamine. Such derivatives may be converted to the ketone by hydrolysis.

When a compound of formula I is prepared in which $R^5$ is OH then that compound may be converted to a compound of formula I wherein $R^5$ is $-O-$ lower alkyl by processes known for lower alkyl etherification (eg. Williamson Synthesis, Merck Index 10th Edition page ONR-96 and references cited therein). For example the lower alkyl ether may be prepared by first forming the alkali metal salt of the alcohol using an alkali metal hydride, then reacting with an alkyl halide, eg. methyl iodide.

Compounds of formula I wherein $R^5$ is hydrogen can be prepared by methods disclosed in UK Patent Specification 1,432,378 or by analogous methods. They may also be prepared by reducing corresponding alcohols using hydrogenation techniques. For example compounds of formula I wherein $R^5$ is OH may be reduced by hydrogenation using palladium charcoal to give the corresponding compound of formula I wherein $R^5$ is hydrogen.

Compounds of formula II which are useful as intermediates are novel compounds within the scope of this invention. Included within these intermediates are those having formula II in which the carbon epi to the nitrogen is protected by one or two organic silyl protecting groups eg. by trialkylsilyl. Accordingly the intermediates can be represented by formula IIa

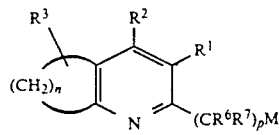 (IIa)

wherein n,p,$R^1,R^2,R^3,R^6$ and $R^7$ are as hereinbefore defined, M is Na, K, Li or MgHal where Hal is a halogen, and $P^1$ and $P^2$ each represent optional organic silyl protecting group on the carbon epi to the nitrogen.

Starting materials for the processes described herein are known compounds or can be prepared by analogous methods for known compounds.

This invention also provides pharmaceutical compositions comprising a compound of formula I or a pharmaceutically acceptable salt thereof.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carrier) is surrounded by carriers, which is thus in association with it. Similarly cachets are included. Sterile liquid form compositions include sterile solutions, suspensions, emulsions, syrups, and elixirs. The active ingredient can be dissolved or suspended in a pharmaceutically acceptable carrier, such a sterile water, sterile organic solvent or a mixture of both. The active ingredients can be often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil. Preferably the pharmaceutical composition is in unit dosage form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more, eg. 25 mg to 250 mg, according to the particular need and the activity of the active ingredient. The invention also includes the compounds in the absence of carrier where the compounds are in unit dosage form. Based on the results from animal studies the dosage range for the treatment of humans using a compound of formula I will be in the range from about 5 mg to 2 g per day depending on the activity of the compound.

The following Examples illustrate the invention and methods for preparing compounds of the invention.

EXAMPLE 1

1-(6,7,8,9-Tetrahydro-3-methyl-5H-cyclohepta[b]pyrid-2-yl)-1-(4-methylphenyl)methanol a) A 1.36M solution of n-butyl lithium in hexane(19 ml) in THF (20 ml) was treated with a solution of 6,7,8,9-tetrahydro-3-methyl-5H-cyclohepta[b]pyridine (4.0 g, 0.025 m) in tetrahydrofuran (THF) (5 ml) at 0° C. After 0.5 hours the solution was blown over, under nitrogen pressure, into a solution of trimethylsilyl chloride (10 ml) in THF (30 ml) cooled to 0° C. After 0.5 hours the solvent was removed under reduced pressure and the residue treated with hexane, filtered and evaporated to give an oil containing 6,7,8,9-tetrahydro-3-methyl-9-trimethylsilyl-5H-cyclohepta[b]pyridine.

b) The oil from step (a) was dissolved in THF (50 ml) and a 1.36M solution of n-butyl lithium in hexane (19 ml) was added at 0° C. The mixture was stirred at this temperature for a further 0.5 hours. 4-Methylbenzaldehyde (3.6 g, 0.03 m) in THF (5 ml) was added rapidly at 0° C. and the mixture stirred for a further 0.25 hours. A solution of 2M hydrochloric acid (60 ml) was added and stirred for 0.25 hours, then separated. The aqueous phase was separated and basified with solid potassium carbonate and then extracted with chloroform. The combined chloroform extracts were washed with water, dried (MgSO$_4$) and evaporated. The residue was treated with ether and the crystallised material collected and dried to give the title compound (2.2 g) m.p. 143°-5° C.

Analysis: Found C, 81.4; H, 8.3; N, 4.7. C$_{19}$H$_{23}$NO requires C, 81.1; H. 8.2; N, 5.0%.

EXAMPLE 2

6,7,8,9-Tetrahydro-3-methyl-2-(4-methylbenzoyl)-5H-cyclohepta[b]pyridine 1-(6,7,8,9-Tetrahydro-3-methyl-5H-cyclohepta[b]pyrid-2-yl)-1-(4-methylphenyl)methanol (2.0 g) (prepared according to Example 1) in toluene (50 ml) with manganese dioxide (6.1 g) was refluxed and water collected in a Dean and Stark apparatus. The cooled solution was filtered and the solvent evaporated under reduced pressure to give a gum. This was dissolved in diethyl ether and treated with ethereal HCl. A solid precipitated and was collected by filtration and dried to give the title compound as the hydrochloride (1.8 g 80%) m.p. 172°-4° C.

Analysis: Found C, 72.1; H. 7.1; N, 4.8 C$_{19}$H$_{21}$NO HCl requires C,72.25; H, 7.0; N, 4.4%.

EXAMPLE 3

1-(6,7,8,9-Tetrahydro-5H-cyclohepta[b]pyrid-2-yl)-1-(4-methylphenyl)methanol 6,7,8,9-Tetrahydro-5H-cyclohepta[b]pyridine (7.4 g 0.05 m) in tetrahydrofuran (100 ml) was cooled to −10° C. and treated with a 1.57M solution of n-butyl lithium in n-hexane (32 ml), then stirred at −10° C. for a further 0.5 hours. 4-Tolualdehyde (10 g 0.083 m) in tetrahydrofuran (10 ml) was added rapidly and the mixture allowed to warm to room temperature, then water and diethyl ether were added. The combined ether extracts were treated with 2N hydrochloric acid and the aqueous acid extract which separated was basified with solid sodium carbonate and then extracted with chloroform. The combined chloroform solutions were washed with water, dried (MgSO$_4$) and evaporated to give an oil. This was purified by chromatography using silica columns eluted with diisopropyl ether or chloroform. The purification was monitored by tlc using diisopropyl ether and chloroform on silica plates or samples were silylated with 1-(trimethylsilyl)imidazole and injected on a g.l.c. (injection temp 200° C.) with a 25 meter BPI column, running a temperature programme from 120° to 300° C. at 10° C./min, then isothermal and carrier gas helium at 10 psi. The title compound having a retention time 17.32 minutes was isolated and converted into the hydrochloride salt by dissolving in diethyl ether and treating with ethereal HCl (1.5 g mp 168°-170° C.).

Analysis: Found C, 70.0; H, 7.4; N, 4.55 C$_{18}$H$_{21}$NO. HCl, 0.25 H$_2$O requires C, 70.1; H, 7.4; N, 4.5%.

EXAMPLE 4

1-(6,7,8,9-Tetrahydro-5H-cyclohepta[b]pyrid-2-yl)-1-phenylmethanol 6,7,8,9-Tetrahydro-3-methyl-5H-cyclohepta[b]pyridine (4.42 g, 0.025 m) in tetrahydrofuran (50 ml) was cooled to −40° C. under nitrogen and treated with n-butyl lithium in n-hexane (1.57 molar soln, 16 ml) and allowed to warm to 0° C. The solution was cooled to −70° C. and treated with a solution of benzaldehyde (4 ml) in tetrahydrofuran (10 ml) and allowed to warm to room temperature, then water and diethyl ether were added. The organic phase was separated and extracted with 2N hydrochloric acid. The acid phase was made basic with solid sodium carbonate and then extracted with chloroform. The combined chloroform extract was washed with water, dried (MgSO$_4$) and evaporated under reduced pressure to give a gum. This was dissolved in n-hexane and the crystallised material collected by filtration. This was purified by chromatograpy on silica using diisopropyl ether: chloroform (9:1 by volume) as eluent. The isolated solid was triturated in diisopropyl ether give 1-(6,7,8,9-tetrahydro-3-methyl-5H -cyclohepta[b]pyrid-2-yl)-1-phenylmethanol (1.1 g) m.p. 130°-2° C.

Analysis: Found C, 80.95; H, 8.2; N, 5.2 C$_{18}$H$_{21}$ NO requires C, 80.9; H, 7.9; N, 5.2%.

EXAMPLE 5

6,7,8,9-Tetrahydro-3-methyl-2-(1-methyloxy-4-methylbenzyl)-5H-cyclohepta[b]pyridine 1-(6,7,8,9-Tetrahydro-3-methyl-5H-cyclohepta[b]pyrid-2-yl)-1-(4-methylphenyl)methanol (2.0 g 0.007 m) was added to sodium hydride (0.35 g, 50% dispersion in oil, 0.007M, washed with 40-60 petrol) suspended in dimethylformamide(20 ml). After evolution of hydrogen had ceased, methyl iodide (0.5 ml) was added and the mixture stirred at room temperature for 0.5 hours. Water was added and the mixture extracted with diethyl ether. The combined ether extracts were treated with 2N hydrochloric acid. The aqueous acid solution was separated, basified with solid sodium carbonate and extracted with chloroform. The combined chloroform extracts were washed with water, dried (MgSO$_4$) and evaporated. The residue was purified by chromatography on silica and eluted with chloroform to give the title compound as a gum. This was dissolved in diethyl ether and treated with ethereal HCl to give the crystalline hydrochloride salt, 1.4 g m.p. 144°–6° C.

Analysis: Found C, 72.1; H, 7.9; N, 4.4 $C_{20}H_{25}NO$. HCl requires C, 72.4; H, 7.9; N, 4.2%.

EXAMPLE 6

1-(6,7,8,9-Tetrahydro-3-methyl-5H-cyclohepta[b]pyrid-2-yl)-1-methyl-1-(4-methylphenyl)methanol To a 1.56M solution of n-butyl lithium in n-hexane (13 ml) in toluene (20 ml) at −20° C. under nitrogen, was added a solution of 2-bromo-3-methyl-6,7,8,9-tetrahydro-5H-cyclohepta[b]pyridine (4.8 g 0.02 m) in toluene (20 ml) and kept at −20° C. for 0.5 hours. A solution of 4′-methylacetophenone (3.0 g 0.022 m) was added and the mixture allowed to warm to room temperature and water added. The organic phase was separated and extracted with 2 N hydrochloric acid. This was basified with solid sodium carbonate, then extracted with chloroform. The combined chloroform extracts were dried (MgSO$_4$) and evaporated under reduced pressure. The residue was purified by chromatography on silica using chloroform as eluent to give a gum. This was dissolved in ether and treated with ethereal HCl to give the title compound as the hydrochloride, three quarter hydrate salt (1.95 g) m.p. 162°–4° C.

Analysis: Found C, 69.2; H, 8.0; N, 4.1 $C_{20}H_{25}NO$ HCl. 0.75H$_2$O requires C, 69.55; H, 7.7, N, 4.1%.

EXAMPLE 7

6,7,8,9-Tetrahydro-3-methyl-2-(4-methylphenyl)-5H-cyclohepta[b]pyridine 1-(6,7,8,9-Tetrahydro-3-methyl-5H-cyclohepta[b]pyrid-2-yl)-1-(4-methylphenyl)methanol (3.0 g) was dissolved in ethanol (150 ml) and added to 10% Pd/C (1 g) under nitrogen. 2M Sulphuric acid (5 ml) was added and the mixture hydrogenated at 50 psi until hydrogen uptake had ceased. The catalyst was removed by filtration and the ethanol removed under reduced pressure. The residue was treated with sodium carbonate solution and then extracted with chloroform. The combined chloroform extracts were dried (MgSO$_4$) and evaporated to give an oil. The product was separated from starting material by purification using an alumina column eluted with chloroform. The resulting oil was dissolved in diethyl ether and acidified with ethereal HCl to give the title compound as the hydrochloride, (0.47 g,) m.p 172°–4° C.

Analysis: Found C, 75.3; H, 7.8; N, 4.4. $C_{19}H_{23}$ N.HCl requires C, 75.6; H, 8.0; N, 4.6%.

EXAMPLE 8

2-(6,7,8,9-Tetrahydro-5H-cyclohepta[b]pyrid-2-yl)-1-4-methylphenyl)ethanol

To a solution of 1.6M n-butyl lithium in n-hexane (7.2 ml) in toluene (25 ml), at −20° C. under nitrogen, was added a solution of 2-methyl-6,7,8,9-tetrahydro-5H-cyclohepta[b]pyridine (1.7 g 0.01 m) in toluene (5 ml). The solution was left to stir at −20° C. for 0.75 hours, then blown over into a solution of 4-methylbenzaldehyde (1.5 g). The solution was allowed to warm to room temperature and water added. The toluene phase was extracted with 2N hydrochloric acid and this was basified with solid potassium carbonate and then extracted with dichloromethane. The combined dichloromethane extracts were washed with water, dried (MgSO$_4$) and evaporated to give an oil. This was purified by chromatography on basic alumina using diisopropyl ether as eluent to give the title compound as an oil. This was dissolved in ether and treated with ethereal HCl to give a crystalline hydrochloride salt (1.2 g) m.p. 184°–6° C.

Analysis: Found C, 71.7; H, 7.6; N, 4.2 $C_{19}H_{23}NO$, HCl requires C, 71.8; 4, 7.6; N, 4.4%.

EXAMPLE 9

1-(6,7,8,9-Tetrahydro-3-methyl-5H-cyclohepta[b]pyrid-2-yl)-1-(4-methylphenyl)methylamine a) To a solution of 1.6M n-butyl lithium in n-hexane (16.5 ml) in toluene (20 ml) at −20° C. under nitrogen was added a solution of 2-bromo-6,7,8,9-tetrahydro-3-methyl-5H-cyclohepta[b]pyridine (6.0 g, 0.02 m) in toluene (30 ml). The reaction mixture was kept at −20° C. for 0.25 hours and then blown over into a solution of 4-methyl benzonitrile (3.2 g) in toluene (30 ml) at −20° C. Then mixture was allowed to warm to room temperature. The solvent was removed under reduced pressure to give 1-(6,7,8,9-tetrahydro-3-methyl-5H-cyclohepta[b]pyrid-2-yl)-1-(4-methylphenyl)methylimine.

b) Ethanol (150 ml) was added to the product of step (a) followed by small portions of sodium borohydride (1.2 g). After stirring at room temperature for 0.75 hours, 2N hydrochloric acid was added until hydrogen evolution had ceased. The solvent was removed under reduced pressure and the residue treated with sodium bicarbonate solution and extracted with chloroform. The combined chloroform extracts were washed with water, dried (MgSO$_4$) and evaporated. The residue was purified by chromatography on basic alumina, eluted with chloroform to give an oil. This was dissolved in diethyl ether and treated with ethereal HCl to give the title compound as the dihydrochloride, monohydrate salt, (1.93 g)m.p. 178°–180° C.

Analysis: Found C, 61.7; H, 7.3; N, 7.8 $C_{19}H_{24}N_2$. 2HCl H$_2$O requires C, 61.45; H, 7.6; N, 7.5%.

EXAMPLE 10

1-(3—Chlorophenyl)-1-(6,7,8,9-tetrahydro-3-methyl-5H-cyclohepta[b]pyrid-2-yl)methanol To a solution of 1.6M n-butyl lithium in n-hexane (16.5 ml) in toluene (20 ml) at −20° C. under nitrogen was added a solution of 2-bromo-6,7,8,9-tetrahydro-3-methyl -5H-cyclohepta[b]pyridine (6.0 g, 0.025 m) in toluene (30 ml). The reaction mixture was kept at −20° C. for 0.25 hours and then blown over into a cooled solution of 3-chlorobenzaldehyde (3.7 g) in toluene (30 ml) at −20° C., and allowed to warm to room temperature. Water was added and the separated organic phase extracted with 2N hydrochloric acid. This was basified with solid potassium carbonate and extracted with chloroform. The combined chloroform extracts were washed with water, dried (MgSO$_4$) and evaporated. The solid was purified by passing through a short silica column, eluted with chloroform, then re-crystallised from diethyl ether to give the title compound (4.31 g) m.p. 123°–5° C.

Analysis: Found C, 71.4; H, 6.8; N, 5.0 $C_{18}H_{20}ClNO$ requires C, 71.6; H, 6.7;N, 4.6%.

EXAMPLE 11

1-(6,7,8,9-Tetrahydro-3-methyl-5H-cyclohepta[b]pyrid-2-yl)-1-(3-methoxyphenyl)methanol To a solution of 1.6M n-butyl lithium in n-hexane (16.5 m,) in toluene (20 ml) at −20°, under nitrogen, was added a solution of 2-bromo-6,7,8,9-tetrahydro-3-methyl 5-H-cyclohepta[b]pyridine (6 g, 0.025 m) in toluene (30 ml). The reaction mixture was kept at −20° C. for 0.25 hours and then blown over into a cooled solution (−20° C.) of 3-methoxybenzaldehyde (3.7 g) in toluene (30 ml) and allowed to warm up to room temperature. Water was added and the organic phase separated and treated with 2N hydrochloric acid. A precipitate formed and this was collected by filtration and treated with sodium carbonate solution, then chloroform. The organic phase was washed with water, dried (MgO$_4$) and evaporated. Trituration with diethyl ether gave 1-(6,7,8,9-tetrahydro-3-methyl-5H-cyclohepta[b]-pyrid-2-yl)-1-(3-methoxyphenyl)methanol (4.42 g, 59%) m.p. 104°-6° C.

Analysis: Found C, 76.9; H, 7.8; N,4.85 C$_{19}$H$_{23}$NO$_2$ requires C, 76.7; H, 7.8; N, 4.7%).

EXAMPLE 12

1-(4-Trifluoromethylphenyl)-1-(6,7,8,9-tetrahydro-3--methyl-5H-cyclohepta[b]pyrid-2-yl)methanol To a solution of 1.6M n-butyl lithium in n-hexane (16.5 ml) in toluene (20 ml) at −20° C., under nitrogen, was added a solution of 2-bromo-6,7,8,9-tetrahydro-3-methyl-5H-cyclohepta[b]pyridine (6.0 g, 0.025 m) in toluen (30 ml). The reaction mixture was kept at −20° C. for 0.25 hours and then blown over into a solution of a,a,a-tri-fluoro-p-tolualdehyde (4.7 g) in toluene (30 ml) at −20° C. The solution was allowed to warm up to room temperature and water added. The organic phase was separated with 2N hydrochloric acid. This was basified with solid potassium carbonate and extracted with chloroform. The combined chloroform extracts were dried (MgSO$_4$) and evaporated. The residue was recrystallised from n-hexane to give the title compound, (5.05 g) m.p. 131°-3° C.

Analysis: Found C, 68.0; H, 5.9; N, 4.5 C$_{19}$H$_{20}$F$_3$NO requires C, 68.05;H, 6.0; N, 4.2%.

EXAMPLE 13

1-(6,7,8,9-Tetrahydro-3-methyl-5H-cyclohepta[b]pyrid-2-yl)-1-(pyrid-3-yl)methanol To a solution of 1.6M n-butyl lithium in n-hexane (16.5 ml) in toluene (20 ml) at −20° C., under nitrogen, was added a solution of 2-bromo-6,7,8,9-tetrahydro-3-methyl-5H-cyclohepta[b]pyridine (6 g, 0.025 m) in toluene (30 ml) and kept at −20° C. for 0.25 hours. This was blown over into a solution of 3-pyridine carboxaldehyde (2.7 g) in toluene (30 ml) kept at −20° C. The solution was allowed to warm up to room temperature and water added. The organic phase was separated, dried (MgSO$_4$) and evaporated. The solid was recrystallised from ether (twice) to give 1-(6,7,8,9-tetrahydro-3-methyl-5H-cyclohepta[b]pyrid-2-yl)-1-(pyrid-3-yl)methanol (4.32 g, 64%) m.p. 124°-6° C.

Analysis Found C,75.8; H, 7.5; N, 10. 4. C$_{17}$H$_{20}$N$_2$O requires C, 76.1; H, 7.5; N, 10.4%.

EXAMPLE 14

1-(6,7,8,9-Tetrahydro-3-methyl-5H-cyclohepta[b]pyrid-2-yl)-1-(thiophen-2-yl)methanol To a solution of 1.6M n-butyl lithium in n-hexane (16.5 ml) in toluene (20 ml) at −70° C., under nitrogen, was added a solution of 2-bromo-6,7,8,9-tetrahydro-3-methyl-5H-cyclohepta[b]pyridine (6 g 0.025 m) and the mixture kept at −20° C. for 0.25 hours. This was blown over into a solution of 2-thiophenecarboxaldehyde (3.0 g) in toluene (30 ml) kept at −20° C., then allowed to warm to room temperature and water added. The organic phase was extracted with 2N hydrochloric acid, then basified with solid potassium carbonate and extracted with chloroform. The combined chloroform extracts were dried (MgSO$_4$) and evaporated. The residue was recrystallised from n-hexane to give the title compound (4.42 g), m.p. 102°-4° C.

Analysis: Found C, 70.4; H, 7.15; N, 5 3 C$_{16}$H$_{19}$NOS requires C, 70.3; H, 7.0; N, 5.1%.

EXAMPLES 15-20

Using a procedure analogous to Example 6 the following compounds of formula I are prepared according to the reaction scheme

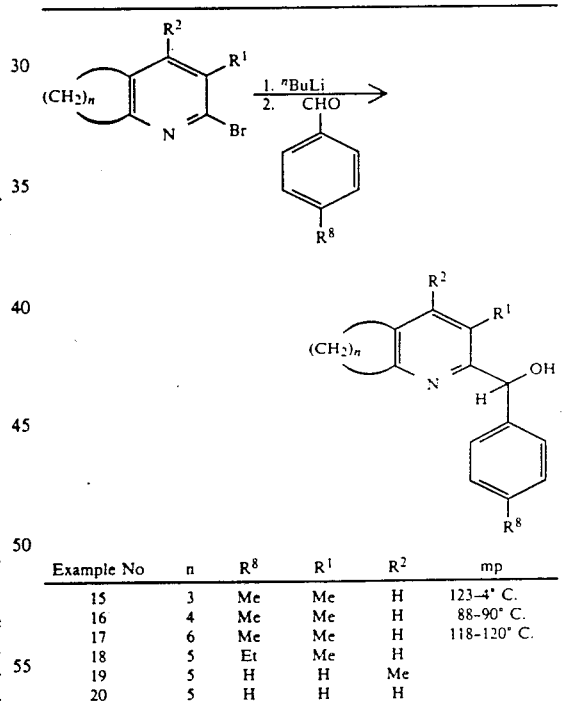

| Example No | n | R$^8$ | R$^1$ | R$^2$ | mp |
|---|---|---|---|---|---|
| 15 | 3 | Me | Me | H | 123-4° C. |
| 16 | 4 | Me | Me | H | 88-90° C. |
| 17 | 6 | Me | Me | H | 118-120° C. |
| 18 | 5 | Et | Me | H | |
| 19 | 5 | H | H | Me | |
| 20 | 5 | H | H | H | |

The following examples illustrate the new route to starting materials of formula (IV) used in some of the aforementioned Examples:

EXAMPLE 21

2—Bromo-3-methyl-6,7,8,9-tetrahydro-5H-cyclohepta[b]pyridine a) Cycloheptanone was converted to an enamine by reaction with pyrrolidine in toluene solvent and in the presence of toluenesulphonic acid. The enamine was alkylated with methacrylonitrile in ethanol solvent and hydrolysed using acetic acid according to the procedure of Stark et al, J. Amer. Chem. Soc., 85, 207 (1963) to give 2-(2-cyanopropyl)cycloheptanone (bp 100° C./0.02 mmHg).

b) The product of step (a) (88 g, 0.5 m) in acetic acid (1l) was treated with bromine (26 ml, 0.5 m) over 15 minutes, maintaining an internal temperature of ca, 15° C. The mixture was allowed to warm to room temperature overnight. The solvent was evaporated off under reduced pressure and the residue partitioned between water and diisopropyl ether. The organic phase was dried (MgSO₄) and evaporated to give a residue which on recrystallising from hexane gave the title compound as white needles, mp 68–70.

EXAMPLES 22–24

By a process analogous to Example 21 using the appropriate cycloalkanone the following compounds of formula IV wherein p is O and Z is Br were prepared:

22. 2-Bromo-3-methyl -5,6,7,8-tetrahydroquinoline, m.p. 50°-2° C.
23. 2-Bromo-3-methyl-5H-cyclopenta[b]pyridine.
24. 2-Bromo-3-methyl-5H-cycloocta[b]pyridine.

As illustrated in Example 21 compounds of formula VII may be prepared from cyclic ketone precursors via enamines by Michael alkylation to introduce the —CHR²CHR¹CN moiety.

We claim:

1. A process for preparing a compound of formula IVa

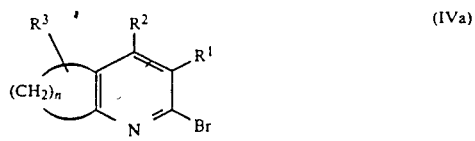

wherein R¹ and R² each independently represent hydrogen, lower alkyl, lower alkoxy, carboxyloweralkyl, carboxy, hydroxyloweralkyl, halogen, haloloweralkyl, lower alkoxycarbonyl, optionally substituted aryl or optionally substituted aralkyl, n represents an integer from 3 to 6, R³ which is optionally present represents single or multiple substitution on one or more of the aliphatic carbons by one or more substituents selected from lower alkyl, optionally substituted aryl and optionally substituted aralkyl, which comprises reacting a compound of formula VII

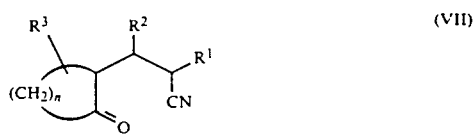

where n, R¹, R² and R³ are as defined above, in an inert solvent with either HBr and bromine or with bromine.

* * * * *